(12) United States Patent
Milus

(10) Patent No.: US 6,855,668 B2
(45) Date of Patent: Feb. 15, 2005

(54) METHODS AND PRODUCTS FOR INHIBITING GROWTH OF FUNGAL PATHOGENS ON TURFGRASS

(75) Inventor: Eugene A. Milus, Fayetteville, AR (US)

(73) Assignee: Board of Trustees of University of Arkansas, Little Rock, AR (US)

( * ) Notice: Subject to any disclaimer, the term of this patent is extended or adjusted under 35 U.S.C. 154(b) by 0 days.

(21) Appl. No.: 10/337,946

(22) Filed: Jan. 7, 2003

(65) Prior Publication Data

US 2004/0132811 A1 Jul. 8, 2004

(51) Int. Cl.[7] .................... A01N 37/34; A01N 37/18; A61K 31/16
(52) U.S. Cl. .................... 504/309; 514/613; 514/626
(58) Field of Search ................ 514/613, 626; 504/309

(56) References Cited

FOREIGN PATENT DOCUMENTS

WO    WO2003092693    * 11/2003

* cited by examiner

*Primary Examiner*—Alton Pryor
(74) *Attorney, Agent, or Firm*—J. M. (Mark) Gilbreth; Mary A. Gilbreth; Gilbreth & Associates, P.C.

(57) ABSTRACT

Methods and products for inhibiting growth of fungus and fungal disease on a plant. Methods comprise contacting at least a portion of a plant or plant seed together with a fungicidal composition comprising a fungicidal carboxamide. Products comprise any of leaves, crowns, roots, stolons, seed, seedlings, sod, and any combination thereof, treated with a fungicidal carboxamide. Preferred pathogens are of the genus *Colletotrichum*, preferred disease is anthracnose, preferred fungicides are carboxamides, and preferred plants are turfgrass.

17 Claims, No Drawings

METHODS AND PRODUCTS FOR INHIBITING GROWTH OF FUNGAL PATHOGENS ON TURFGRASS

BACKGROUND OF THE INVENTION

1. Field of the Invention

The present invention relates to methods and products for inhibiting growth of fungus and fungal disease on plants. In another aspect, the present invention relates to methods and products for inhibiting fungus and fungal growth on turfgrass. In even another aspect, the present invention relates to methods and products for inhibiting anthracnose on turfgrass. In yet another aspect, the present invention relates to methods and products for inhibiting anthracnose on bentgrass and bluegrass. In even yet another aspect, the present invention relates to methods and products for inhibiting growth of *Colletotrichum* on bentgrass turf.

2. Description of the Related Art

The control of plant diseases caused by fungal pathogens is a great concern in a large variety of botanical and agricultural areas such as, for example, production and maintenance of ornamental plants, turfgrass, vegetables, grain, and fruit crops. Overcoming fungal growth and disease are important for achieving optimal plant growth, development and production.

A great deal of time, energy and money are put into the production and maintenance of turfgrass. Maintaining healthy turfgrass is of interest to consumers not only for private residences, but also for businesses. Perhaps the most noticeable business market for turfgrass is the golf industry wherein grounds keepers strive to maintain expanses of flawless, healthy green turf.

Turfgrass, in addition to numerous other plants and crops, is susceptible to anthracnose disease. Anthracnose is found in many areas and climates and attacks most turfgrasses but is most damaging on Annual Bluegrass (*Poa annua*) and Creeping Bentgrass (*Agrostis palistris*) in North America.

The fungal pathogen of anthracnose in turfgrass is *Colletotrichum graminicola*. The fungus is an active pathogen of young leaves but it is most readily detected on senescent plant parts. The pattern of anthracnose symptoms depends largely on weather conditions. Rotting of the basal stem is the most prevalent symptom detected during cool, wet weather. Water-soaked stem lesions become dark in color and the leaf blades eventually yellow and die. The central stem can be pulled from the plant quite easily revealing a blackened base.

Reddish-brown lesions may occur when warm weather, dry soil and increased humidity surround the turf canopy. Reddish-brown irregular patterns on the turf may form as the disease develops. Over time, the patterns turn yellow, tan, then brown.

Keeping the turf healthy and reducing stress, for example, by soil compaction, may help in reducing the damage observed on the plant material. Proper watering and correcting fertilizer deficiencies, especially phosphorus and potassium, are also sometimes helpful in reducing damage caused by *Colletotrichum graminicola*.

Fungicidal products are also available for treating anthracnose in turfgrass. However, in spite of conventional fungicides and treatment methods, the need exists for fungicidal compounds and products which are efficient in inhibiting growth of fungal pathogens, are less costly, are less toxic, and are environmentally safe.

SUMMARY OF THE INVENTION

The present invention relates to methods and products comprising use of fungicidal compounds and compositions. The compounds and compositions are useful for inhibiting growth of a fungal pathogen and fungal disease. The methods and products are generally used for establishing and/or maintaining healthy turfgrass.

One embodiment of the present invention is directed to a method for inhibiting the growth of a fungal pathogen on turfgrass. Generally the method comprises the step of a) contacting at least a portion of a turfgrass with an effective amount of a fungicidal compound of formula I,

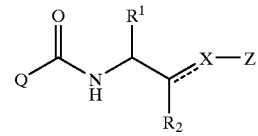

wherein
Q is

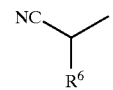

Z is

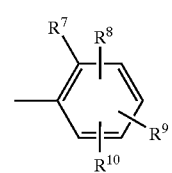

X is —O—, —CH($R^{11}$)— or =C($R^{11}$)—;
$R^1$ is H or $CH_3$;
$R^2$ is H or $CH_3$;
$R^6$ is $C_2$–$C_6$ alkyl, $C_{,2}$–$C_6$ alkenyl, $C_2$–$C_6$ alkynyl or $C_3$–$C_6$ cycloalkyl each optionally substituted with halogen or CN;
$R^7$ is H, CN, halogen, $C_1$–$C_4$ haloalkyl, $C_1$–$C_4$ alkyl, $C_2$–$C_4$ alkenyl or $C_2$–$C_4$ alkynyl each optionally substituted with halogen or CN;
$R^8$, $R^9$ and $R^{10}$ are each independently H, halogen, CN, $C_1$–$C_3$ alkyl, $C_1$–$C_3$ haloalkyl, $SCF_2H$, $SCF_3$ or $Si(CH_3)_3$; and
$R^{11}$ is H, $C_1$–$C_5$ alkyl, $C_2$–$C_5$ alkenyl or $C_2$–$C_5$ alkynyl.

Another embodiment of the present invention is directed to a method for inhibiting the growth of a fungal pathogen on turfgrass. Generally the method comprises the step of a) contacting at least a portion of a turfgrass with an effective amount of a fungicidal composition comprising a compound of formula I.

Even another embodiment of the present invention is directed to a treated turfgrass product wherein at least a portion of the product has been contacted with a fungicidally effective amount of a compound of formula I.

Still another embodiment of the present invention is directed to a treated turfgrass product wherein at least a portion of the product has been contacted with a fungicidally effective amount of a composition comprising a compound of formula I.

Yet another embodiment of the present invention is directed to a method of making a pathogen-resistant turfgrass product comprising the step of a) contacting at least a portion of a turfgrass element together with a fungicidally effective amount of a compound of formula I.

DETAILED DESCRIPTION OF THE INVENTION

The present invention is directed to methods and products for inhibiting growth of fungal pathogens on a plant. The methods and products of the invention utilize a fungicidal compound of Formula I (including all geometric and stereo isomers), agricultural compositions containing them, and their use as fungicides:

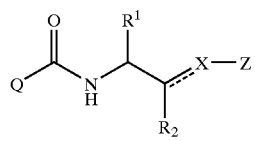

I wherein

Q is

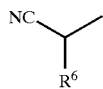

Z is

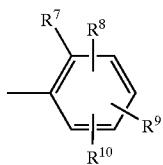

X is —O—, —CH($R^{11}$)— or =C($R^{11}$)—;

$R^1$ is H or $CH_3$;

$R^2$ is H or $CH_3$;

$R^6$ is $C_2$–$C_6$ alkyl, $C_2$–$C_6$ alkenyl, $C_2$–$C_6$ alkynyl or $C_3$–$C_6$ cycloalkyl each optionally substituted with halogen or CN;

$R^7$ is H, CN, halogen, $C_1$–$C_4$ haloalkyl, $C_1$–$C_4$ alkyl, $C_2$–$C_4$ alkenyl or $C_2$–$C_4$ alkynyl each optionally substituted with halogen or CN;

$R^8$, $R^9$ and $R^{10}$ are each independently H, halogen, CN, $C_1$–$C_3$ alkyl, $C_1$–$C_3$ haloalkyl, $SCF_2H$, $SCF_3$ or $Si(CH_3)_3$; and $R^{11}$ is H, $C_1$–$C_5$ alkyl, $C_2$–$C_5$ alkenyl or $C_2$–$C_5$ alkynyl.

In the above recitations, the term "alkyl" includes straight-chain or branched alkyl, such as, methyl, ethyl, n-propyl, i-propyl, or the different butyl, pentyl or hexyl isomers. The term "alkyl," used alone includes straight-chain or branched alkyl, such as, methyl, ethyl, n-propyl, i-propyl, or the different butyl, pentyl or hexyl isomers. "Alkenyl" includes straight-chain or branched alkenes such as vinyl, 1-propenyl, 2-propenyl and the different butenyl, pentenyl, hexenyl, heptenyl, octenyl, nonenyl and decenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl, hexynyl, heptynyl, octynyl, nonynyl and decynyl isomers. "Alkynyl" can also include moieties comprised of multiple triple bonds such as 2,5-hexadiynyl. "Cycloalkyl" includes, for example, cyclopropyl, cyclobutyl, cyclopentyl and cyclohexyl.

The term "halogen," either alone or in compound words such as "haloalkyl," includes fluorine, chlorine, bromine or iodine. Further, when used in compound words such as "haloalkyl," said alkyl may be partially or fully substituted with halogen atoms which may be the same or different. Examples of "haloalkyl" include $F_3C$, $ClCH_2$, $CF_3CH_2$ and $CF_3CCl_2$.

The total number of carbon atoms in a substituent group is indicated by the "$C_i$–$C_j$" prefix where i and j are numbers from 1 to 6. For example, $C_1$–$C_3$ alkyl designates methyl through propyl. When a group contains a substituent which can be hydrogen, for example $R^1$ or $R^3$, then, when this substituent is taken as hydrogen, it is recognized that this is equivalent to said group being unsubstituted.

Compounds of the present invention can exist as one or more stereo isomers. The various stereo isomers include enantiomers, diastereomers, atropisomers and geometric isomers. One skilled in the art will appreciate that one stereo isomer may be more active and/or may exhibit beneficial effects when enriched relative to the other stereo isomer(s) or when separated from the other stereo isomer(s). Additionally, the skilled artisan knows how to separate, enrich, and/or to selectively prepare said stereo isomers. Accordingly, the present invention comprises compounds selected from Formula I. The compounds of the invention may be present as a mixture of different isomers.

In preferred compounds of Formula I useful in the methods and products of the present invention, X is O; $R^1$ is H or $CH_3$; $R^2$ is H or $CH_3$; $R^6$ is $C_2$–$C_6$ alkyl, $C_2$–$C_6$ alkenyl, $C_2$–$C_6$ alkynyl or $C_3$–$C_6$ cycloalkyl each optionally substituted with halogen or CN; $R^7$ is H; $R^8$ is halogen; $R^9$ is H; and $R^{10}$ is halogen. A particularly preferred compound useful in the methods and products of the present invention is rel-2-cyano-N-[(1R)-2-(2,5-difluorophenoxy)-1-methylethyl]-3,3-dimethylbutanimide and has the following structure:

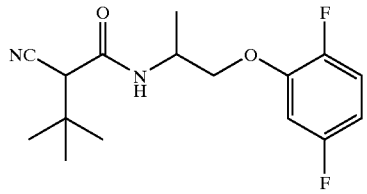

The methods and products of the present invention are useful for inhibiting the growth of any fungal organism, and/or fungal disease, on any host plant. Preferred fungal pathogens are of the *Colletotrichum* genus. The genus *Colletotrichum* is a member of the order Melanconiales of the class *Coelomycetes*. In a particularly preferred embodiment of the invention, the targeted fungal pathogen is *Colletotrichum graminicola*. Preferably the disease is anthracnose.

In the present invention, preferably the plant is any turfgrass. More preferably the turfgrass is a bluegrass or a bentgrass. Suitable bluegrasses includes Annual Bluegrass (*Poa annua*), Kentucky bluegrass (*Poa pratensis*), Rough bluegrass (*Poa trivialis* L.), Supina bluegrass (*Poa supina*), Canada bluegrass (*Poa compressa* L.). Suitable bentgrasses include Creeping Bentgrass (*Agrostis palustris*) such as the "Penncross" cultivar, Colonial bentgrass (*Agrostis*

*capillaris*), Dryland bentgrass (*Agrostis castellena*), and Velvet bentgrass (*Agrostis canina*). Of the above listed turfgrasses, the main hosts for anthracnose are annual bluegrass and bentgrass, thus they are the most preferred plants of the present invention.

Compounds useful in the present invention may be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation. Techniques for preparing formulations/compositions useful in the present invention are well known to one of ordinary skill in the art. Preferably, formulations used in the methods and products of the present invention are ultimately in a liquid form and applied to the target plant by spraying.

The formulations will typically contain effective amounts of active ingredient having Formula I, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-Soluble Granules, Tablets and Powders | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High strength Compositions | 90–99 | 0–10 | 0–2 |

Typical solid diluents are described in Watkins, et al., *Handbook of Insecticide Dust Diluents and Carriers*, $2^{nd}$ Ed., Dorland Books, Caldwell, N.J. typical liquid diluents are described in Marsden, *Solvents Guide*, $2^{nd}$ Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, ground corn cobs, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Compounds useful in the present invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimenol, tricyclazole, triticonazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

The method and products of the present invention are useful in controlling plant diseases and fungal pathogens. The methods and products of the present invention comprise contacting at least a portion of a plant, with an effective amount of a fungicidal compound or fungicidal composition comprising said compound. The methods and products of the present invention are useful either pre- or post-infection. Thus, the methods and products of the invention may be used as either preventative treatments or curative treatments. The portion of a plant to be contacted with the compounds and/or compounds useful in the invention include, for example, leaves, crowns, roots, stolons, stems, foliage, fruit, seeds, seedlings, tubers or bulbs, and the media (soil or sand) in which the plants to be protected are growing or are to be grown. Particularly preferred turfgrass portions include leaves, crowns, stolons, roots and any combination thereof.

Treatments may be carried out daily, weekly or monthly. Any treatment schedule may be followed as long as optimal inhibition of fungal growth fungal disease is obtained. Preferably treatments are performed about once every 14 to 28 days. In the methods and products of the present invention, the step of contacting the fungicidal compounds and/or compositions may be carried out by any of the techniques known in the art. A preferred contacting method useful in the methods and products of the present invention is spraying. Generally the treatments are applied in the range of about 1 to about 5 gallons per 1000 square feet, preferably from about 2 to about 4 gallons per 1000 square feet. Generally the concentration of active ingredient (ai) is in the range of from about 0.5 to about 10.0 grams per 1000 square feet of area to be treated, preferably in the range of about 1 to about 3 grams per 1000 square feet. In a particularly preferred embodiment of the invention, the active ingredient is used at a concentration of 2.5 grams in 4 gallons per 1000 square feet.

Another contacting method known in the art useful for the methods and products of the present invention is to apply the fungicidal compounds and/or compositions of the present invention onto granules such as, for example, granules of crushed corn cob or clay. Generally the active ingredient is applied at a concentration in the range of about 0.5–5.0% by weight, preferably at about 1.0% by weight, per 1000 square feet. Techniques for preparing granule formulations are known in the art and all such techniques are applicable herein.

As known by one of skill in the art, the contacting step may be optimized by a subsequent watering step or steps. The watering step may help to optimally contact the fungicide with the plant.

One embodiment of the present invention is directed to a method for inhibiting the growth of a fungal pathogen on turfgrass. Generally the method comprises the step of a) contacting at least a portion of a turfgrass with an effective amount of a fungicidal compound of formula I. A preferred compound is rel-2-cyano-N-[(1R)-2-(2,5-difluorophenoxy)-1-methylethyl]-3,3-dimethylbutanamide. The at least a portion of the turfgrass may be any turfgrass "element" selected from the group consisting of turfgrass sod, turfgrass seed, turfgrass seedlings, turfgrass roots, leaves, stolon, crowns, and any combination thereof. Generally the turfgrass is afflicted with anthracnose caused by at least one member of the genus *Colletotrichum*. More particularly, the anthracnose is caused by *Colletotrichum graminicola*. Preferably the turfgrass is bentgrass, more preferably creeping bentgrass.

Another embodiment of the present invention is directed to a method for inhibiting the growth of a fungal pathogen on turfgrass. Generally the method comprises the step of a) contacting at least a portion of a turfgrass with an effective amount of a fungicidal composition comprising a compound of formula I. A preferred compound is rel-2-cyano-N-[(1R)-2-(2,5-difluorophenoxy)-1-methylethyl]-3,3-dimethylbutanamide. The at least a portion of a turfgrass may be any turfgrass "element" selected from the group consisting of leaves, crowns, roots, stolon, seed, seedlings, and any combination thereof. Generally the turfgrass is afflicted with anthracnose caused by at least one member of the genus *Colletotrichum*. More particularly, the anthracnose is caused by *Colletotrichum graminicola*. Preferably the turfgrass is bentgrass, more preferably creeping bentgrass.

Still another embodiment of the present invention is directed to a treated turfgrass product wherein at least a portion of the product has been contacted with a fungicidally effective amount of a compound of formula I. A preferred compound is rel-2-cyano-N-[(1R)-2-(2,5-difluorophenoxy)-1-methylethyl]-3,3-dimethylbutanamide. Generally the turfgrass product is selected from the group consisting of turfgrass sod, turfgrass seed, turfgrass seedlings, turfgrass roots, and any combination thereof. Preferably the product is resistant to anthracnose disease. In a particularly preferred embodiment, the product is resistant anthracnose caused by *Colletotrichum graminicola*. Preferably the turfgrass is bentgrass, more preferably creeping bentgrass.

Still another embodiment of the present invention is directed to a treated turfgrass product wherein at least a portion of the product has been contacted with a fungicidally effective amount of a composition comprising a compound of formula I. A preferred compound is rel-2-cyano-N-[(1R)-2-(2,5-difluorophenoxy)-1-methylethyl]-3,3-dimethylbutanamide. Generally the turfgrass product is selected from the group consisting of sod, seed, seedlings, leaves, crowns, stolons, roots, and any combination thereof. Preferably the product is resistant to anthracnose disease. For protection against anthracnose in turfgrass, preferred elements are leaves, crowns, roots, stolon, sod, and any combination thereof. In a particularly preferred embodiment, the product is resistant to anthracnose caused by *Colletotrichum graminicola*.

Yet another embodiment of the present invention is directed to a method of making a pathogen-resistant turfgrass product comprising the step of a) contacting at least a portion of a turfgrass element together with a fungicidally effective amount of a compound of formula I. The compound may be in a composition. A preferred compound is rel-2-cyano-N-[(1R)-2-(2,5-difluorophenoxy)-1-methylethyl]-3,3-dimethylbutanamide. The turfgrass "element" may be any of the group consisting of leaves, crowns, roots, stolon, seed, seedlings, sod, and any combination thereof. For protection against anthracnose in turfgrass, preferred elements are leaves, crowns, roots, stolon, sod, and any combination thereof. In a particularly preferred embodiment, the product is resistant to anthracnose caused by *Colletotrichum graminicola*.

EXAMPLES

The invention having been generally described, the following example is provided merely to illustrate one embodiment of the invention. It is understood that the example is given by way of illustration and is not intended to limit the specification or the claims in any manner.

Example 1

Evaluation of Fungicides for Control of Anthracnose on Bentgrass Putting Greens The test was established on the 16$^{th}$ green at the Fianna Hills Country Club in Fort Smith, Ark. The green is more than 20 years old and was maintained at 0.156-inch mowing height and with other standard practices used at Fianna Hills. The design was a randomized complete block with 20 treatments and four replications. Individual plots were 4 feet×5 feet and isolated with a spray shield during applications. Treatments were applied on approximate 14- or 28-day schedules. Actual dates of applications were 31 May, 13 Jun., 27 Jun., 12 Jul., 26 Jul., and 9 Aug., all in 2002. Treatments were applied at 4 gal/1000 sq ft using a hand-held $CO_2$-powered sprayer at 20 psi with a TeeJet 8004VS spray tip. The amount of active ingredient per 1000 square feet for each fungicide is provided in Table I. The C3 biocontrol is a strain of *Lysobacter enzymogenes* that was supplied by Dr. Gary Yuen from the University of Nebraska. The MX 567 active ingredient was first dissolved in acetone and then diluted with water. Treatments were evaluated by recording disease incidence, disease intensity, and turf quality.

The agents tested/utilized in Example 1 are as follows: BAS 500 and 50503 are experimental fungicides and are in the same class as Heritage; CL 3336 and Spectro 90 are well-known, conventional, broad-spectrum fungicides conventionally recommended against anthracnose and other diseases; Endorse is a new product comprising as an active ingredient an antibiotic from a bacterium; Nature Safe, Companion, Banner Maxx, CL3336 were selected by the superintendent at Fianna Hills; Heritage is a conventional first choice fungicide for controlling anthracnose in bentgrass but in this example the pathogen exhibits Heritage-resistance; The C3 biocontrol *L. enzymogenes* strain has been reported to control anthracnose on annual bluegrass turf; Lynx is a experimental fungicide in the same class as Banner Maxx and is known to have activity against anthracnose; MX567 is a compound of the present invention having formula I; and Nontreated checks #1 and #2 are untreated control samples.

Heritage belongs to a family of fungicides that affect electron transport in the targeted fungal pathogen. Banner belongs to a family of fungicides that affect sterol synthesis in the targeted fungal pathogen, and MX567 belongs to a family of fungicides that function by inhibiting melanin biosynthesis in the targeted fungal pathogen.

Disease first became evident on 26 Jun. 2002. As seen in Table I, Spectro 90, Endorse, BAS 500UKF, Lynx+Daconil Ultrex, and MX 567 provide significant reductions in disease severity and increases in turf quality. MX 567 provides the highest turf quality. The pathogen at this location appears to be resistant to Heritage, BAS 50503F, and CL 3336 because disease severities for these treatments are similar to the "nontreated check #1 and #2" samples. The results provided by the C3 biocontrol are similar to those provided by the "nontreated check #1 and #2" samples (i.e., negative controls).

TABLE I

| Product and rate per 1000 sq ft | Application timing (days) | Incidence (%)[a] | | | | Intensity[b] | | Severity[c] | | Turf quality[d] |
|---|---|---|---|---|---|---|---|---|---|---|
| | | Jul. 16 | Jul. 26 | Aug. 2 | Aug. 19 | Aug. 2 | Aug. 19 | Aug. 2 | Aug. 19 | Aug. 19 |
| BAS 500UKF 20 WG 0.5 oz | 0, 13, 27, 42, 56, 70 | 21 | 9 | 45 | 36 | 1.3 | 1.5 | 53 | 48 | 4.8 |
| BAS 500UKF 20 WG 0.9 oz | 0, 27, 56 | 12 | 12 | 36 | 34 | 1.8 | 1.8 | 74 | 72 | 4.3 |
| BAS 500UKF 20 WG 0.5 oz | 0, 27, 56 | | | | | | | | | |
| Concorde 82.5 WG 3.2 oz | 13, 42, 70 | 17 | 3 | 28 | 36 | 1.0 | 1.0 | 28 | 36 | 5.8 |
| BAS 500UKF 20 WG 0.5 oz | 0, 27, 56 | | | | | | | | | |
| T-methyl 540 SC 2 fl oz | 13, 42, 70 | 16 | 21 | 36 | 41 | 1.8 | 2.5 | 69 | 113 | 3.5 |
| BAS 50503F 50 WG 0.2 oz | 0, 13, 27, 42, 56, 70 | 19 | 23 | 60 | 50 | 2.3 | 2.5 | 138 | 130 | 2.8 |
| BAS 50503F 50 WG 0.2 oz | 0, 27, 56 | 15 | 9 | 50 | 60 | 1.8 | 2.8 | 83 | 173 | 3.3 |
| CL 3336 50 WP 6 oz | 0, 13, 27, 42, 56, 70 | 23 | 29 | 64 | 60 | 2.5 | 3.3 | 158 | 198 | 2.3 |
| CL 3336 50 WP 6 oz + Alliance 3 fl oz | 0, 13, 27, 42, 56, 70 | 31 | 35 | 65 | 59 | 2.3 | 3.3 | 148 | 194 | 2.5 |
| Spectro 90 WDG 4 oz | 0, 13, 27, 42, 56, 70 | 29 | 8 | 36 | 34 | 1.0 | 1.3 | 36 | 52 | 5.3 |
| Spectro 90 WDG 4 oz + Alliance 3 fl oz | 0, 13, 27, 42, 56, 70 | 29 | 3 | 19 | 19 | 1.0 | 1.0 | 19 | 19 | 5.5 |
| Endorse 2.5 WP 4 oz | 0, 13, 27, 42, 56, 70 | 26 | 7 | 31 | 23 | 1.0 | 1.5 | 31 | 34 | 4.8 |
| Endorse 2.5 WP 6 oz | 0, 13, 27, 42, 56, 70 | 24 | 7 | 45 | 23 | 1.0 | 1.3 | 45 | 30 | 5.0 |
| Nature Safe (0.5 lbs N) | 0, 27, 56 | | | | | | | | | |
| Companion 4 fl oz | 13, 42, 70 | 36 | 36 | 65 | 45 | 2.0 | 2.5 | 130 | 119 | 3.3 |
| Banner MAXX 2 fl oz | 0, 13 | | | | | | | | | |
| CL 3336 4 oz | 27, 56 | | | | | | | | | |
| Heritage 0.4 oz | 42, 70 | 10 | 13 | 43 | 33 | 1.3 | 2.0 | 46 | 65 | 4.0 |
| Heritage 50 WG 0.4 oz | 0, 27, 56 | 17 | 17 | 40 | 45 | 2.0 | 2.5 | 80 | 110 | 3.5 |
| C3 biocontrol 4 gal of 43% broth culture | 0, 13, 27, 42, 56, 70 | 40 | 39 | 69 | 65 | 3.0 | 3.8 | 211 | 248 | 2.0 |
| Lynx 45 WP 0.28 oz + Daconil Ultrex 82.5 WG 3.2 oz | 0, 13, 27, 42, 56, 70 | 21 | 8 | 33 | 35 | 1.0 | 1.5 | 33 | 55 | 4.5 |
| MX 567 2.5 g ai + .05% Tween | 0, 13, 27, 42, 56, 70 | 21 | 2 | 23 | 29 | 1.0 | 1.0 | 23 | 29 | 6.3 |
| Nontreated check #1 | — | 40 | 41 | 65 | 59 | 3.0 | 3.0 | 200 | 195 | 2.5 |

TABLE I-continued

| Product and rate per 1000 sq ft | Application timing (days) | Incidence (%)[a] | | | | Intensity[b] | | Severity[c] | | Turf quality[d] |
|---|---|---|---|---|---|---|---|---|---|---|
| | | Jul. 16 | Jul. 26 | Aug. 2 | Aug. 19 | Aug. 2 | Aug. 19 | Aug. 2 | Aug. 19 | Aug. 19 |
| Nontreated check #2 | — | 24 | 29 | 55 | 55 | 2.0 | 2.5 | 115 | 145 | 3.3 |
| LSD (P = 0.05) | | 18 | 16 | 26 | 26 | 1.0 | 1.0 | 71 | 96 | 1.4 |

[a]Percentage of plot area with anthracnose symptoms
[b]0 = no disease, 1 = chlorotic, 2 = slight to moderate thinning, 3 = severe thinning, and 4 = dead
[c]incidence × intensity
[d]0–9 rating scale: 0 = all dead, 9 = excellent turf color and density While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

All references cited herein, including research articles, all U.S. and foreign patents and patent applications, are specifically and entirely incorporated by reference.

I claim:

1. A method for inhibiting the growth of a fungal pathogen on turfgrass, wherein the method comprises the step of:
   a) contacting at least a portion of a turfgrass element with an effective amount of a fungicidal compound of formula I

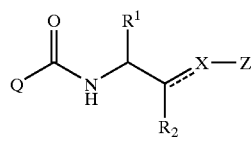

I wherein
Q is

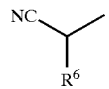

Z is

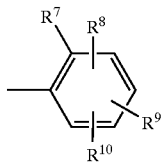

X is —O—, —CH($R^{11}$)— or =C($R^{11}$)—;
$R^1$ is H or $CH_3$;
$R^2$ is H or $CH_3$;
$R^6$ is $C_2$–$C_6$ alkyl, $C_2$–$C_6$ alkenyl, $C_2$–$C_6$ alkynyl or $C_3$–$C_6$ cycloalkyl each optionally substituted with halogen or CN;
$R^7$ is H, CN, halogen, $C_1$–$C_4$ haloalkyl, $C_1$–$C_4$ alkyl, $C_2$–$C_4$ alkenyl or $C_2$–$C_4$ alkynyl each optionally substituted with halogen or CN;
$R^8$, $R^9$ and $R^{10}$ are each independently H, halogen, CN, $C_1$–$C_3$ alkyl, $C_1$–$C_3$ haloalkyl, $SCF_2H$, $SCF_3$ or $Si(CH_3)_3$; and
$R^{11}$ is H, $C_1$–$C_5$ alkyl, $C_2$–$C_5$ alkenyl or $C_2$–$C_5$ alkynyl.

2. The method of claim 1 wherein said turfgrass is afflicted with anthracnose.

3. The method of claim 2 wherein said anthracnose is caused by at least one member of the genus *Colletotrichum*.

4. The method of claim 3 wherein said at least one member is *Colletotrichum graminicola*.

5. The method of claim 2 wherein said turfgrass is bentgrass.

6. The method of claim 5 wherein said bentgrass is creeping bentgrass.

7. The method of claim 5 wherein said compound is rel-2-cyano-N-[(1R)-2-(2,5-difluorophenoxy)-1-methylethyl]-3,3-dimethylbutanamide.

8. The method of claim 1 wherein said element is selected from the group consisting of leaves, crowns, stolons, roots, seed, seedlings, and any combination thereof.

9. A method for inhibiting growth of a fungal pathogen on turfgrass, wherein the method comprises the step of:
   a) contacting at least a portion of a turfgrass element with an effective amount of a fungicidal composition comprising an effective amount of a fungicidal compound of formula I,

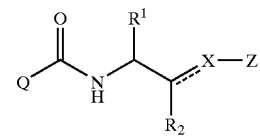

I wherein
Q is

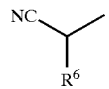

Z is

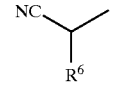

X is —O—, —CH($R^{11}$)— or =C($R^{11}$)—;
$R^1$ is H or $CH_3$;
$R^2$ is H or $CH_3$;

$R^6$ is $C_2$–$C_6$ alkyl, $C_2$–$C_6$ alkenyl, $C_2$–$C_6$ alkynyl or $C_3$–$C_6$ cycloalkyl each optionally substituted with halogen or CN;

$R^7$ is H, CN, halogen, $C_1$–$C_4$ haloalkyl, $C_1$–$C_4$ alkyl, $C_2$–$C_4$ alkenyl or $C_2$–$C_4$ alkynyl each optionally substituted with halogen or CN;

$R^8$, $R^9$ and $R^{10}$ are each independently H, halogen, CN, $C_1$–$C_3$ alkyl, $C_1$–$C_3$ haloalkyl, $SCF_2H$, $SCF_3$ or $Si(CH_3)_3$; and $R^{11}$ is H, $C_1$–$C_5$ alkyl, $C_2$–$C_5$ alkenyl or $C_2$–$C_5$ alkynyl.

10. The method of claim 9 wherein said turfgrass is afflicted with anthracnose.

11. The method of claim 10 wherein said anthracnose is caused by at least one member of the genus *Colletotrichum*.

12. The method of claim 11 wherein said at least one member is *Colletotrichum graminicola*.

13. The method of claim 10 wherein said turfgrass is bentgrass.

14. The method of claim 13 wherein said bentgrass is creeping bentgrass.

15. The method of claim 13 wherein said compound is rel-2-cyano-N-[(1R)-2-(2,5-difluorophenoxy)-1-methylethyl]-3,3-dimethylbutanamide.

16. The method of claim 9 wherein said turfgrass element is selected from the group consisting of leaves, roots, crowns, stolons, sod, seed, seedlings, and any combination thereof.

17. The method of claim 9 wherein said composition further comprises an effective amount of a diluent.

* * * * *